(12) United States Patent
Kim et al.

(10) Patent No.: US 12,089,850 B2
(45) Date of Patent: Sep. 17, 2024

(54) HEMOSTATIC DEVICE (71) Applicant: THE CATHOLIC UNIVERSITY OF KOREA INDUSTRY-ACADEMIC COOPERATION FOUNDATION, Seoul (KR)

(72) Inventors: Sa Jin Kim, Seoul (KR); Jae Eun Shin, Seoul (KR)

(73) Assignee: THE CATHOLIC UNIVERSITY OF KOREA INDUSTRY-ACADEMIC COOPERATION, Seoul (KR)

( * ) Notice: Subject to any disclaimer, the term of this patent is extended or adjusted under 35 U.S.C. 154(b) by 353 days.

(21) Appl. No.: 17/630,298

(22) PCT Filed: Jul. 29, 2021

(86) PCT No.: PCT/KR2021/009842
§ 371 (c)(1),
(2) Date: Jan. 26, 2022

(87) PCT Pub. No.: WO2022/025649
PCT Pub. Date: Feb. 3, 2022

(65) Prior Publication Data
US 2022/0361891 A1 Nov. 17, 2022

(30) Foreign Application Priority Data
Jul. 31, 2020 (KR) .................. 10-2020-0095849

(51) Int. Cl.
A61B 17/12 (2006.01)
A61B 17/42 (2006.01)
A61M 25/10 (2013.01)

(52) U.S. Cl.
CPC ... *A61B 17/12136* (2013.01); *A61M 25/1002* (2013.01); *A61M 25/10181* (2013.11);
(Continued)

(58) Field of Classification Search
CPC .... A61B 17/12136; A61B 2017/12004; A61B 2017/4216; A61B 17/12;
(Continued)

(56) References Cited

U.S. PATENT DOCUMENTS 5,505,698 A * 4/1996 Booth ............... A61M 25/1002
604/103.11
2006/0058831 A1* 3/2006 Atad ................. A61M 25/1002
606/193

(Continued)

FOREIGN PATENT DOCUMENTS

CN 201341907 11/2009
JP 2007511242 5/2007
(Continued)

Primary Examiner — Kelly J Bekker
Assistant Examiner — Andrew P. Restaino
(74) Attorney, Agent, or Firm — NORTON ROSE FULBRIGHT US LLP (57) ABSTRACT A hemostatic device is disclosed. The hemostatic device according to an embodiment of the present invention includes: a balloon which is expanded by a fluid supplied therein; a blood discharge pipe which includes a blood inflow hole at one end and exposes the other end to a lower side of the balloon wherein a certain section of a lower side of the blood inflow hole is surrounded by the balloon; and a fluid flow pipe communicating with the inside of the balloon for supplying or discharging the fluid and extending to a lower side of the balloon. The balloon includes a plurality of protrusions that are formed to protrude outward when the balloon is expanded by the fluid.

9 Claims, 8 Drawing Sheets (52) U.S. Cl.
CPC .............. *A61B 2017/12004* (2013.01); *A61B 2017/4216* (2013.01); *A61M 2025/1086* (2013.01)

(58) Field of Classification Search
CPC ........ A61B 2017/00557; A61B 17/135; A61B 17/42; A61M 25/1002; A61M 25/10181; A61M 2025/1086; A61M 25/0068; A61M 2210/1433; A61M 25/007; A61M 2025/1052; A61M 2025/1061; A61M 2025/1093; A61M 2025/1095; A61M 25/10; A61M 29/02; A61M 27/00
See application file for complete search history.

(56) References Cited

U.S. PATENT DOCUMENTS

| | | | |
|---|---|---|---|
| 2009/0099560 A1* | 4/2009 | Rioux | A61M 25/1011 606/41 |
| 2014/0221980 A1* | 8/2014 | Rontal | A61M 1/77 604/98.01 |
| 2017/0281915 A1* | 10/2017 | Jalgaonkar | A61M 25/1011 |
| 2019/0216297 A1* | 7/2019 | Rentschler | A61M 25/1002 |

FOREIGN PATENT DOCUMENTS

| | | |
|---|---|---|
| KR | 101156229 | 6/2012 |
| KR | 101787280 | 10/2017 |
| KR | 101903591 | 10/2018 |
| KR | 102165620 | 10/2020 |

* cited by examiner

HEMOSTATIC DEVICE

CROSS-REFERENCE TO RELATED APPLICATIONS

This application is a national phase application under 35 U.S.C. § 371 of International Application No. PCT/KR2021/009842, filed Jul. 29, 2021, which claims priority to and the benefit of Korean Patent Application No. 10-2020-0095849, filed Jul. 31, 2020. The contents of the referenced patent applications are incorporated into the present application by reference.

BACKGROUND

Field of the Disclosure

The present invention relates to a hemostatic device, and more particularly, to a hemostatic device for hemostasis by compressing an intrauterine bleeding site of a woman.

Description of Related Art

Most of the complications that occur during childbirth are related to postpartum hemorrhage. In general, postpartum hemorrhage can be defined as a case where postpartum red blood cell volume decreases by 10% or more or a blood transfusion is required. Causes of postpartum hemorrhage include uterine relaxation, upper or lower genital damage, residual pregnancy products, invasive placental shape, uterine rupture, and coagulation disorders. It is known that about 80% of postpartum hemorrhage is due to uterine relaxation, and early postpartum hemorrhage due to uterine relaxation occurring within 24 hours after childbirth accounts for most of the maternal mortality and prevalence.

In order to prevent complications due to hypovolemia when postpartum hemorrhage occurs, measures such as securing blood vessels quickly, administering fluids, and replenishing blood are necessary. In addition to this, if uterine hemorrhage continues, intrauterine hemostasis is required.

Conventionally, a balloon catheter is used for intrauterine hemostasis. The balloon catheter is inserted into the bleeding uterus and expanded to compress the bleeding site to stop the hemorrhage. However, the conventional balloon catheter is not completely in close contact with the inner side of the uterus even if it is expanded in the uterus, so that sufficient compression and hemostasis cannot be performed in many cases. In addition, the conventional balloon catheter is expanded by the saline solution injected therein, and the injection pipe for the saline solution injection is extended to the lower side of the balloon. Therefore, during cesarean section, it is difficult for a surgeon to place a balloon catheter in the uterus and inject saline solution in the state of incision at the surgical site, there is a risk of infection, and there is a cumbersome problem in that it requires assistance from others.

The above information disclosed in this Background section is only for enhancement of understanding of the background of the invention and it may therefore contain information that does not form the prior art that is already known to a person of ordinary skill in the art.

(Patent Document 1) Korean Patent No. 10-1352037 (publication of registration: 2014. 01. 22)

SUMMARY OF THE INVENTION

One aspect of the present invention is directed to providing a hemostatic device that can be disposed in a bleeding uterus and effectively in close contact with the inside of the uterus in a state in which it is expanded by a fluid.

Another aspect of the present invention is directed to provide a hemostatic device capable of being easily injected a fluid through a surgical incision site in a state disposed in the uterus during a cesarean section.

According to an aspect of the present invention, provided is a hemostatic device including: a balloon which is expanded by a fluid supplied therein; a blood discharge pipe which includes a blood inflow hole at one end and exposes the other end to a lower side of the balloon wherein a certain section of a lower side of the blood inflow hole is surrounded by the balloon; and a fluid flow pipe communicating with the inside of the balloon for supplying or discharging the fluid and extending to a lower side of the balloon, wherein the balloon includes a plurality of protrusions that are formed to protrude outward when the balloon is expanded by the fluid.

In this case, the protrusion may be formed to have a hemispherical shape in an expanded state of the balloon.

In addition, the protrusion may be formed to have a polygonal shape in an expanded state of the balloon.

In addition, the plurality of protrusions may be formed to have a honeycomb shape in an expanded state of the balloon.

In addition, the balloon may include a concave portion to be formed between the plurality of protrusions to allow blood to pool and coagulate when the balloon is expanded by the fluid.

In addition, an upper section of the fluid flow pipe may be disposed inside the balloon and a plurality of micropores communicating with the inside of the balloon may be provided in the upper section of the fluid flow pipe.

In addition, the hemostatic device may further include an auxiliary fluid injection pipe communicating with the inside of the balloon for supply of the fluid and extending upward of the balloon.

In addition, the auxiliary fluid injection pipe may have an openable and closeable injection part at a portion extending upwardly of the balloon.

In addition, the injection part may have an injection hole formed to be opened upwardly at a portion extending upwardly of the balloon and a cap for opening and closing the injection hole.

In addition, the balloon may include a wide portion formed to expand outwardly larger than the upper portion when the balloon is expanded by the fluid.

In addition, the wide portion may be formed in a ratio of 1/2 to 2/3 based on the height of the balloon in a state in which the balloon is expanded by the fluid.

In addition, the fluid flow pipe may be disposed in contact with one side of the blood discharge pipe over a certain section from the inside of the balloon and from the lower end of the balloon to the lower side.

According to an embodiment of the present invention, compression and hemostasis of a bleeding site in the uterus can be efficiently performed through the balloon having a plurality of protrusions that are formed to protrude from the outer surface to the outside when the balloon is expanded by a fluid.

According to an embodiment of the present invention, since an auxiliary fluid injection pipe is provided and a fluid can be injected into the balloon by accessing the auxiliary fluid injection pipe through a surgical incision while the hemostatic device is disposed in the uterus during cesarean section operation, the usability of the hemostatic device during surgery is improved.

BRIEF DESCRIPTION OF THE DRAWINGS

The above and other aspects, features, and advantages of the present invention will become more apparent to those of ordinary skill in the art by describing embodiments thereof in detail with reference to the accompanying drawings, in which.

DETAILED DESCRIPTION OF THE EMBODIMENTS

Hereinafter, exemplary embodiments of the present invention will be described in detail so that those of ordinary skill in the art can readily implement the present invention with reference to the accompanying drawings. The present invention may be embodied in many different forms and is not limited to the embodiments set forth herein. In the drawings, parts unrelated to the description are omitted for clarity. Throughout the specification, like reference numerals denote like elements.

It is understood that the terms "comprise" or "have" when used in this specification, are intended to describe the presence of stated features, integers, steps, operations, members, components and/or a combination thereof but not preclude the possibility of the presence or addition of one or more other features, integers, steps, operations, members, components, or a combination thereof.

In this specification, spatially relative terms "front", "rear", "upper or above or top" or "lower or below or bottom" may be used to describe a correlation with the elements shown in the drawings. These are relative terms determined based on what is shown in the drawings, and the positional relationship may be conversely interpreted according to the orientation.

The presence of an element in/on "front", "rear", "upper or above or top" or "lower or below or bottom" of another element includes not only being disposed in/on "front", "rear", "upper or above or top" or "lower or below or bottom" directly in contact with other elements, but also cases in which another element being disposed in the middle, unless otherwise specified. In addition, unless otherwise specified, that an element is "connected" to another element includes not only direct connection to each other but also indirect connection to each other.

Figure 1:
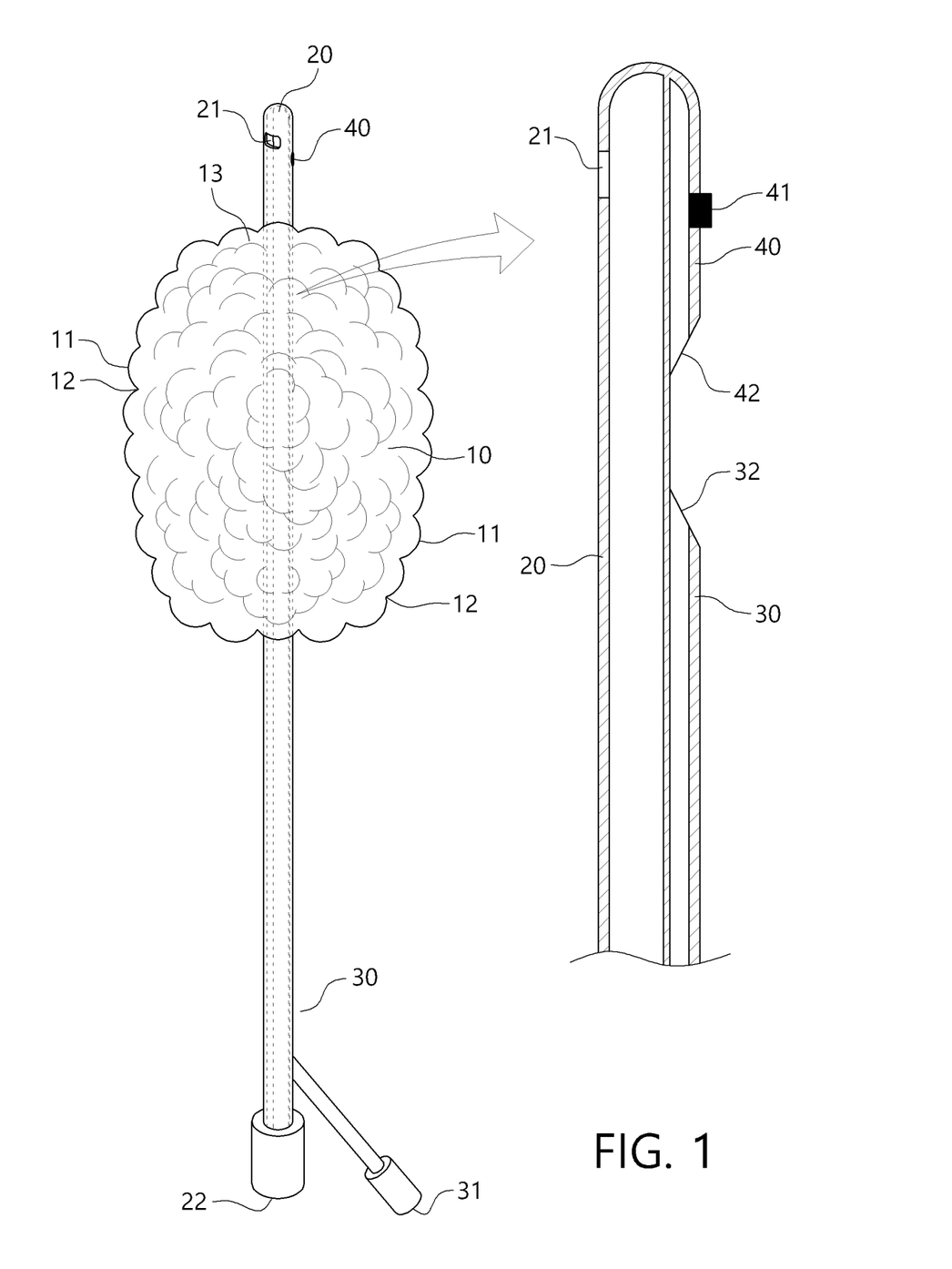
FIG. 1 is a configuration diagram of a hemostatic device according to a first embodiment of the present invention.
Figure 2:
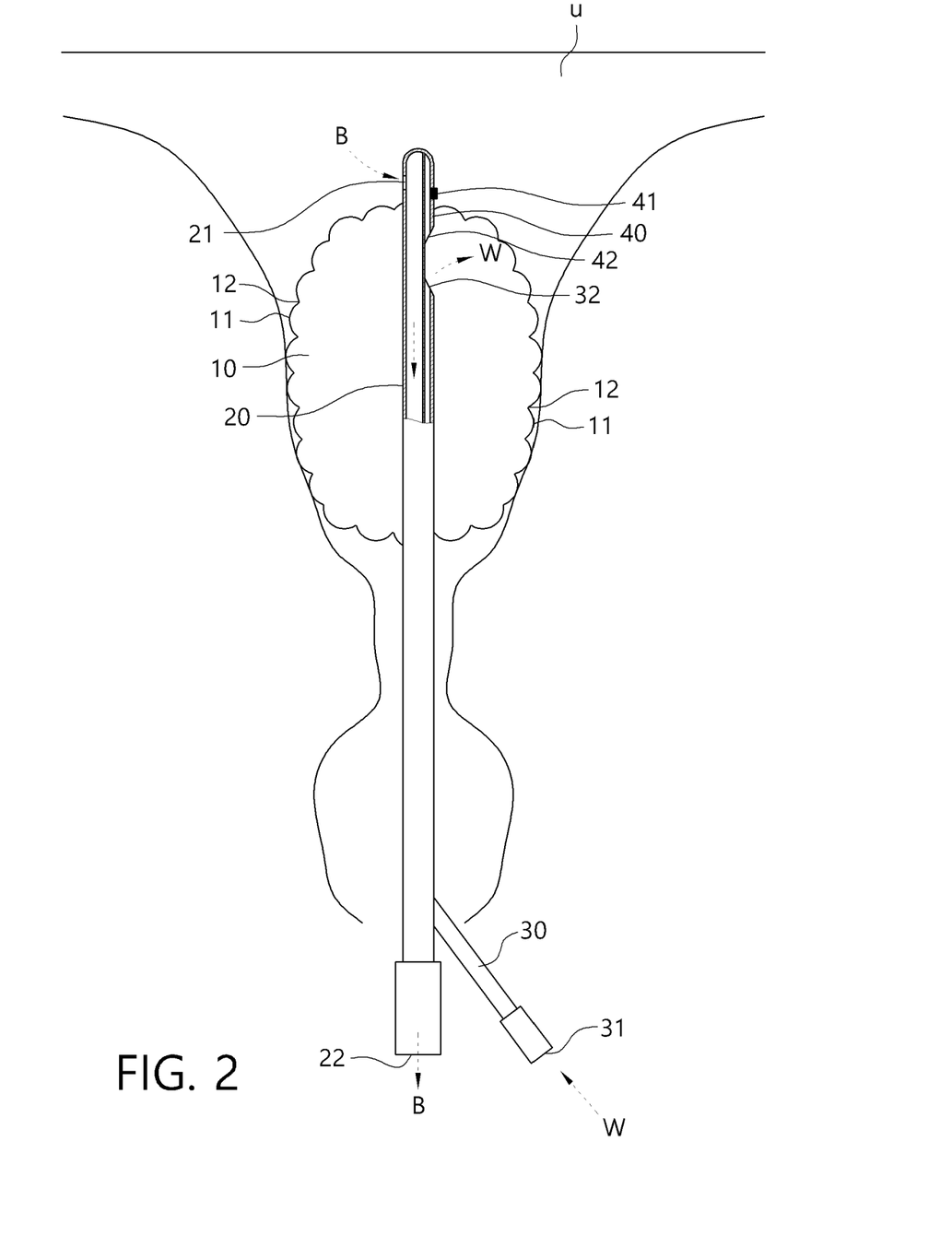
FIG. 2 is a diagram illustrating a first use state of the hemostatic device according to the first embodiment of the present invention.

FIG. 1 is a configuration diagram of a hemostatic device according to a first embodiment of the present invention. FIG. 2 is a diagram illustrating a first use state of the hemostatic device according to the first embodiment of the present invention. In addition, FIG. 3 is a diagram illustrating a second use state of the hemostatic device according to the first embodiment of the present invention.

Figure 3:
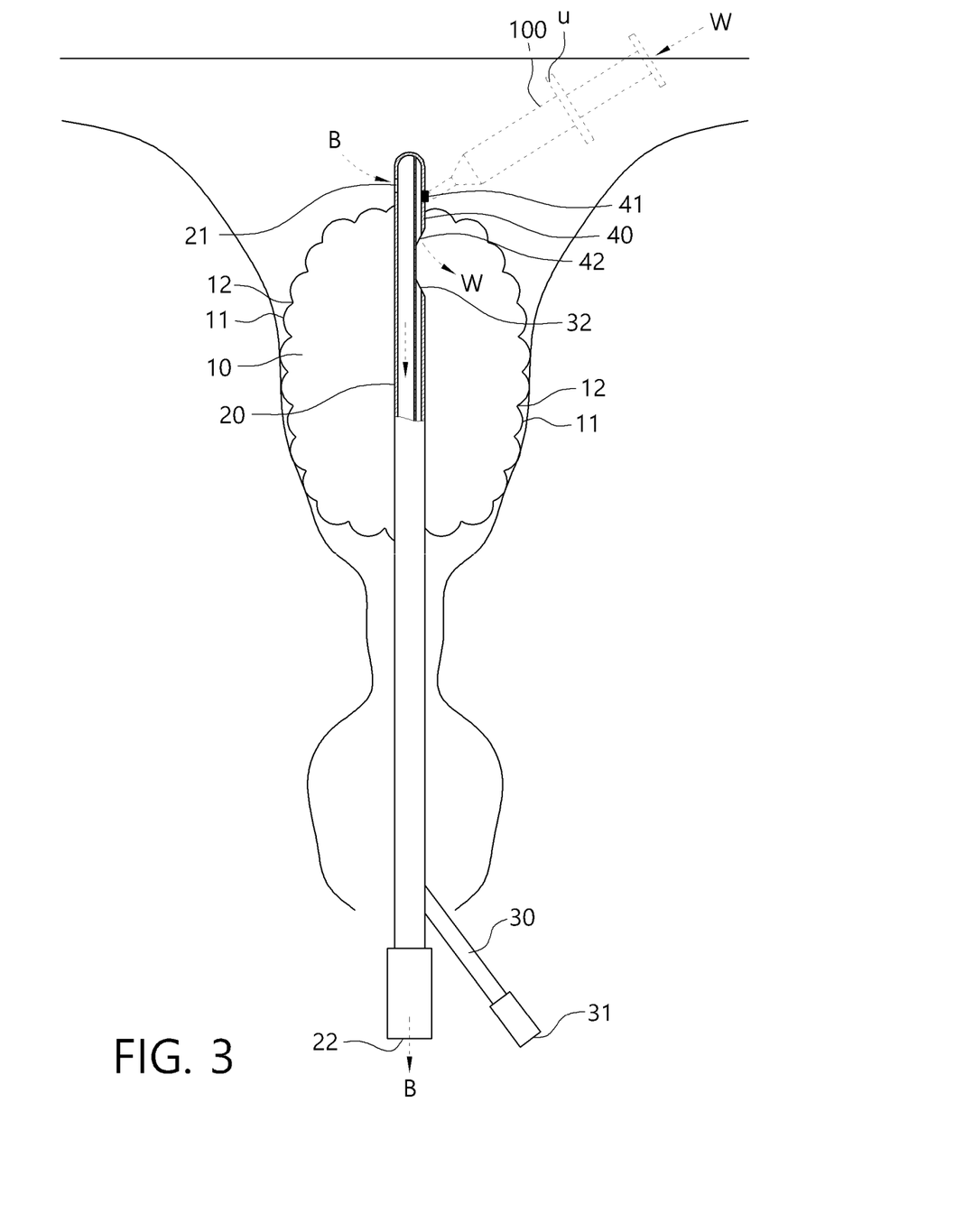
FIG. 3 is a diagram illustrating a second use state of the hemostatic device according to the first embodiment of the present invention.

Referring to FIGS. 1 to 3, the hemostatic device according to the first embodiment of the present invention is for performing hemostasis when hemorrhage occurs in the uterus U due to postpartum hemorrhage or the like. The hemostatic device according to the first embodiment of the present invention may be disposed in the uterus U to induce blood discharge and coagulation while compressing the bleeding site inside the uterus U.

The hemostatic device according to the first embodiment of the present invention includes a balloon 10, a blood discharge pipe 20, a fluid flow pipe 30, and an auxiliary fluid injection pipe 40.

Hereinafter, each configuration of the hemostatic device according to the first embodiment of the present invention will be described in detail.

The balloon 10 is expanded by a fluid W supplied therein. In other words, the balloon 10 has a fluid accommodation space capable of accommodating the fluid W therein. The balloon 10 may be made of a medical silicone material that can expand and contract. The balloon 10 may be expanded by the fluid W supplied in a state disposed in the uterus U to compress the inside of the uterus U. In this case, the fluid W may be physiological saline solution.

In the first embodiment of the present invention, the balloon 10 is formed to have an ellipsoidal shape in the expanded state. For efficient compression on the inner side of the uterus (U), the balloon 10 preferably has a shape similar to the shape of the space within the uterus U of the woman.

In the first embodiment of the present invention, the balloon 10 includes a plurality of protrusions 11 that are formed to protrude from the outer surface to the outside when the balloon is expanded by the fluid W. More specifically, according to the first embodiment of the present invention, each of the protrusions 11 may be formed to have a hemispherical shape in the expanded state.

The plurality of protrusions 11 may be uniformly formed on the outer surface of the balloon 10. However, if necessary, it may be considered that a plurality of protrusions 11 are intensively formed on the side portion of the balloon 10 that is in close contact with the inner side of the uterus U and performs compression. In addition, the protrusion 11 may not be provided at a portion of the outer surface of the balloon 10 that is not in close contact with the inner side of the uterus U.

When the balloon 10 is expanded by the fluid W, the plurality of protrusions 11 additionally protrude from the outer surface of the balloon 10 and are in close contact with the inside of the uterus U to perform hemostasis. When the balloon 10 is expanded by the fluid W, the plurality of protrusions 11 are additionally protruded, so that the outer surface of the balloon 10 has an overall uneven shape.

If the outer surface of the balloon 10 is formed smoothly, it is difficult to be fully in closed contact with the inside of the uterus U of the patient in a state in which the balloon 10 is expanded. If a contact area between the balloon 10 and the inner side of the uterus U is not sufficiently secured, the compressive force for hemostasis may be insufficient, and the hemostatic effect may be reduced.

However, according to the first embodiment of the present invention, when the balloon 10 is expanded by the fluid W, a plurality of protrusions 11 provided in the balloon 10 are additionally protruded to the outside to be in close contact with the inside of the uterus U. Through this, a contact area between the balloon 10 and the inner side of the uterus U can be sufficiently secured, and hemostasis through compression can be effectively achieved.

In addition, the plurality of protrusions 11 increase the grip force on the contact area and prevent slipping. Accordingly, it is possible to prevent the balloon 10 from unintentionally escaping out of the uterus U of the patient during the hemostasis process.

In addition, in the first embodiment of the present invention, the balloon 10 includes concave portions 12 formed between the plurality of projections 11. In other words, when the balloon 10 is expanded by the fluid, a plurality of concave portions 12 may be formed between the plurality of protrusions 11. The concave portion 12 may provide a space between the plurality of protrusions 11 in which the blood B may pool and coagulate.

Figure 4:
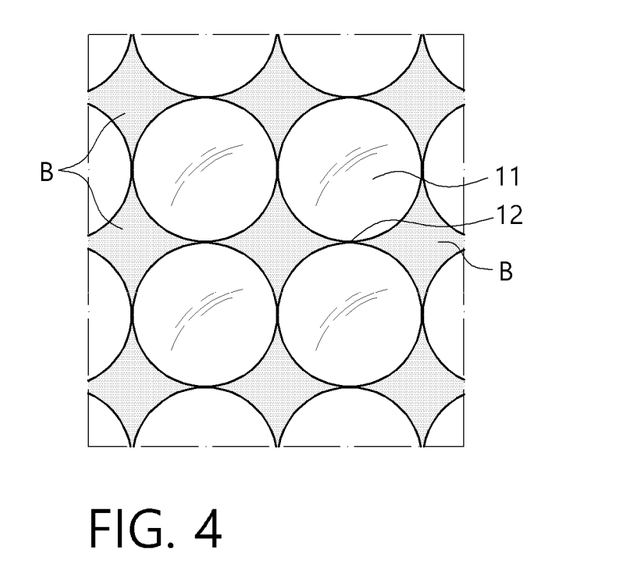
FIG. 4 is a diagram illustrating functions of protrusions and concave portions of the hemostatic device according to the first embodiment of the present invention.

FIG. 4 is a diagram illustrating functions of protrusions and concave portions of the hemostatic device according to the first embodiment of the present invention.

Referring to FIG. 4, in the expanded state of the balloon 10, the plurality of protrusions 11 are in close contact with the inner side of the uterus U to perform compression. In this case, the concave portion 12 provides a space between the plurality of protrusions 11 in which the blood B may pool and coagulate. That is, the blood B flowing out in the process of compressing through the protrusion 11 may pool in the concave portion 12 and coagulate. Accordingly, hemostasis can be achieved while minimizing the discharge of blood.

As shown in FIG. 4, when a plurality of protrusions 11 are formed adjacent to each other, the concave portion 12 formed between several adjacent protrusions 11 may be formed to be disconnected from other adjacent concave portions 12. In this way, when individual concave portions 12 are formed by being disconnected, it may contain the blood B more efficiently.

In addition, it may be considered that the central portion of the concave portion 12 is relatively more concave in the expanded state of the balloon 10 so that the blood B is more efficiently contained in the concave portion 12.

Figure 5:
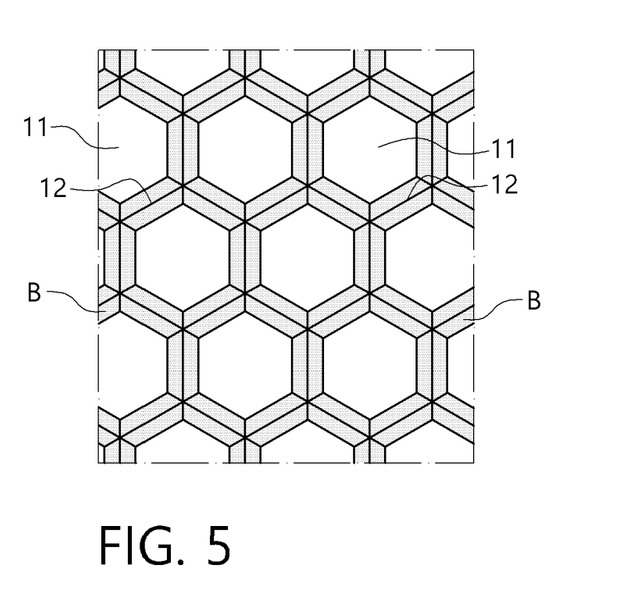
FIG. 5 is a diagram illustrating an example and function of modifications of protrusions and concave portions of the hemostatic device according to the first embodiment of the present invention.

FIG. 5 is a diagram illustrating an example and function of modifications of protrusions and concave portions of the hemostatic device according to the first embodiment of the present invention.

In the first embodiment of the present invention, the shapes of the protrusion 11 and the concave portion 12 may be variously modified. Referring to FIG. 5, the protrusion 11 may be formed in a polygonal shape. In more detail, in the modified example shown in FIG. 5, the protrusion 11 has a hexagonal shape.

Meanwhile, in the first embodiment of the present invention, a plurality of protrusions 11 may be formed to have an overall honeycomb shape in the expanded state of the balloon 10. In other words, the plurality of protrusions 11 and the concave portions 12 formed therebetween may form an overall honeycomb shape in the expanded state of the balloon 10.

Of course, the shapes of the protrusion 11 and the concave portion 12 are not limited to the first embodiment of the present invention and its modifications. The protrusion 11 may have any number of different shapes on the premise that the protrusion is additionally protruded in the expanded state of the balloon 10 so that it can be in close contact with the inner side of the uterus U. Accordingly, the shape of the concave portion 12 may also be variously modified.

The blood discharge pipe 20 is formed to include a blood inflow hole 21 at one end and expose the other end to a lower side of the balloon 10 wherein a certain section of a lower side of the blood inflow hole 21 is surrounded by the balloon 10. That is, the blood discharge pipe 20 is disposed in a form in which a certain section of an upper side thereof is surrounded by the balloon 10.

The blood inflow hole 21 of the blood discharge pipe 20 may be formed in various shapes. For example, the blood inflow hole 21 may be formed as a long hole formed on the outer circumference surface of the blood discharge pipe 20. In addition, two or more blood inflow holes 21 may be formed along the circumferential direction of the blood discharge pipe 20. Meanwhile, the blood inflow hole 21 may be formed of a plurality of micropores.

As shown in FIGS. 2 and 3, in the process of using the hemostatic device according to the first embodiment of the present invention, one end of the blood discharge pipe 20 is disposed in the uterus U of the patient together with the balloon 10, and a certain section of the other end is exposed to the outside of the patient's body. Therefore, some of the blood B bleeding in the uterus U may flow into the inside of the blood discharge pipe 20 through the blood inflow hole 21 formed at one end of the blood discharge pipe 20, and the blood B introduced into the blood discharge pipe 20 may move downward and be discharged to the outside of the patient's body through the blood outlet 22 formed at the other end of the blood discharge pipe 20. In this case, the blood outlet 22 may be formed with an enlarged diameter for the smooth discharge of blood.

The fluid flow pipe 30 communicates with the inside of the balloon 10 for supply or discharge of the fluid W and extends downward of the balloon 10. The upper section of the fluid flow pipe 30 may be disposed inside the balloon 10. In addition, the fluid flow pipe 30 may be disposed in contact with one side of the blood discharge pipe 20 over a certain section from the inside of the balloon 10 and from the lower end of the balloon 10 to the lower side. In a state in which the hemostatic device is disposed in the uterus U of the patient, a certain section of the lower portion of the fluid flow pipe 30 is exposed to the outside of the patient's body.

When open surgery is not performed or when a hemostatic device is used after surgery is completed, the fluid flow pipe 30 can make it possible to supply the fluid W from the outside of the patient's body to the inside of the balloon 10 disposed in the uterus U of the patient. Of course, depending on circumstances, the injection of the fluid W through the fluid flow pipe 30 may be made even in the open surgery process.

In a state in which the hemostatic device according to the first embodiment of the present invention is disposed in the uterus U of the patient, a first inlet/outlet 31 for the inflow and outflow of the fluid W is formed at the end of the fluid flow pipe 30 exposed to the outside of the patient's body. In addition, a second inlet/outlet 32 is formed at the opposite end communicating with the inside of the balloon 10. In this case, the first inlet/outlet 31 may be formed with an enlarged diameter for effective coupling with a valve (not shown) for opening and closing a flow path, a device for injecting the fluid W, and the like.

Referring to FIG. 2, in a state in which the hemostatic device is disposed in the uterus U of the patient, when the balloon 10 is expanded, the fluid W may be injected through the first inlet/outlet 31 of the fluid flow pipe 30. The fluid W injected through the first inlet/outlet 31 of the fluid flow pipe 30 proceeds into the balloon 10 through the second inlet/outlet 32 of the fluid flow pipe 30, and expands the balloon 10.

When the injection of the fluid W is completed and the balloon 10 is sufficiently expanded, the first inlet/outlet 31 is closed. The first inlet/outlet 31 may be closed through a valve (not shown) or the like coupled to the first inlet/outlet 31.

Meanwhile, when the fluid W is excessively introduced into the balloon 10 or hemostasis is completed, or when the hemostatic device needs to be removed from the patient's body after the hemostatic device is placed, if necessary, the fluid W inside the balloon 10 may be discharged through the second inlet/outlet 32 of the fluid flow pipe 30. The fluid entering the fluid flow pipe 30 through the second inlet/outlet 32 of the fluid flow pipe 30 may be discharged to the outside through the first inlet/outlet 31 of the fluid flow pipe 30.

The auxiliary fluid injection pipe 40 communicates with the inside of the balloon 10 for supply of the fluid W and extends upward of the balloon 10. A certain section of the lower portion of the auxiliary fluid injection pipe 40 may be disposed inside the balloon 10, and a certain section of the upper portion may be disposed above the balloon 10.

The auxiliary fluid injection pipe 40 includes an openable and closeable injection part 41 at a portion extending upwardly of the balloon 10. In addition, an outlet 42 communicating with the inside of the balloon 10 is formed on the lower side of the auxiliary fluid injection pipe 40.

In the first embodiment of the present invention, the injection part 41 may include an injection hole formed on the outer circumference surface of a portion extending upwardly of the balloon 10 of the auxiliary fluid injection pipe 40 and a stopper provided in a form that can be opened and closed at the injection hole. As shown in FIG. 3, when the fluid W injection into the injection part 41 is made through a fluid supply device 100 (e.g., a syringe), the stopper may be formed to be opened when connected to the fluid supply device 100 and closed when the fluid supply device 100 is disconnected.

In addition, in consideration of the input pressure of the fluid W, the injection part 41 may be provided while extending the auxiliary fluid injection pipe 40 from the outer circumference surface to the outside by a predetermined length. That is, the auxiliary fluid injection pipe 40 has a portion extending a predetermined length to the outside from the outer circumference surface, and the injection hole of the injection part 41 is formed in the extended portion, and it may also be contemplated that a stopper as described above is disposed at the injection hole.

Meanwhile, the auxiliary fluid injection pipe 40 may be disposed in contact with one side of the blood discharge pipe 20. In this case, the injection part 41 may be disposed below the blood inflow hole 21.

If there is no auxiliary fluid injection pipe 40 and a situation requiring hemostasis occurs during cesarean section, the hemostatic device according to the first embodiment of the present invention is placed in the patient's uterus U and then the fluid W should be supplied through the aforementioned fluid flow pipe 30 in order to inject the fluid W to expand the balloon 10. However, the fluid flow pipe 30 is formed so that the lower section is exposed to the outside of the patient's body through the lower part of the patient's uterus U, and the fluid W may be injected through the first inlet/outlet 31 formed on the exposed end side of the fluid flow pipe 30. Therefore, the distance between the surgical site and the fluid W injection part is long, so the convenience of use in the surgical process is reduced, and there is also a risk of infection.

However, the hemostatic device according to the first embodiment of the present invention includes a separate auxiliary fluid injection pipe 40. Accordingly, as shown in FIG. 3, during cesarean section, the fluid supply device 100 (e.g., a syringe) may directly access the auxiliary fluid injection pipe 40 through the resected surgical site, and after opening the injection part 41 of the auxiliary fluid injection pipe 40, the fluid W may be injected into the balloon 10 to expand the balloon 10, and then the injection part 41 may be closed.

As such, the auxiliary fluid injection pipe 40 makes it possible to inject the fluid W into the balloon 10 through the resected surgical site during a surgical operation. Therefore, the surgeon performing the operation can use the hemostatic device more easily and conveniently without the risk of infection.

Even when the fluid W is injected through the auxiliary fluid injection pipe 40, when the hemostatic device is removed after hemostasis, the fluid W may be discharged to the outside through the fluid flow pipe 30 as described above.

Meanwhile, in the first embodiment of the present invention, the blood discharge pipe 20, the fluid flow pipe 30, and the auxiliary fluid injection pipe 40 may be made of a medical silicone material. Further, the blood discharge pipe 20, the fluid flow pipe 30, and the auxiliary fluid injection pipe 40 may have flexibility.

Figure 6:
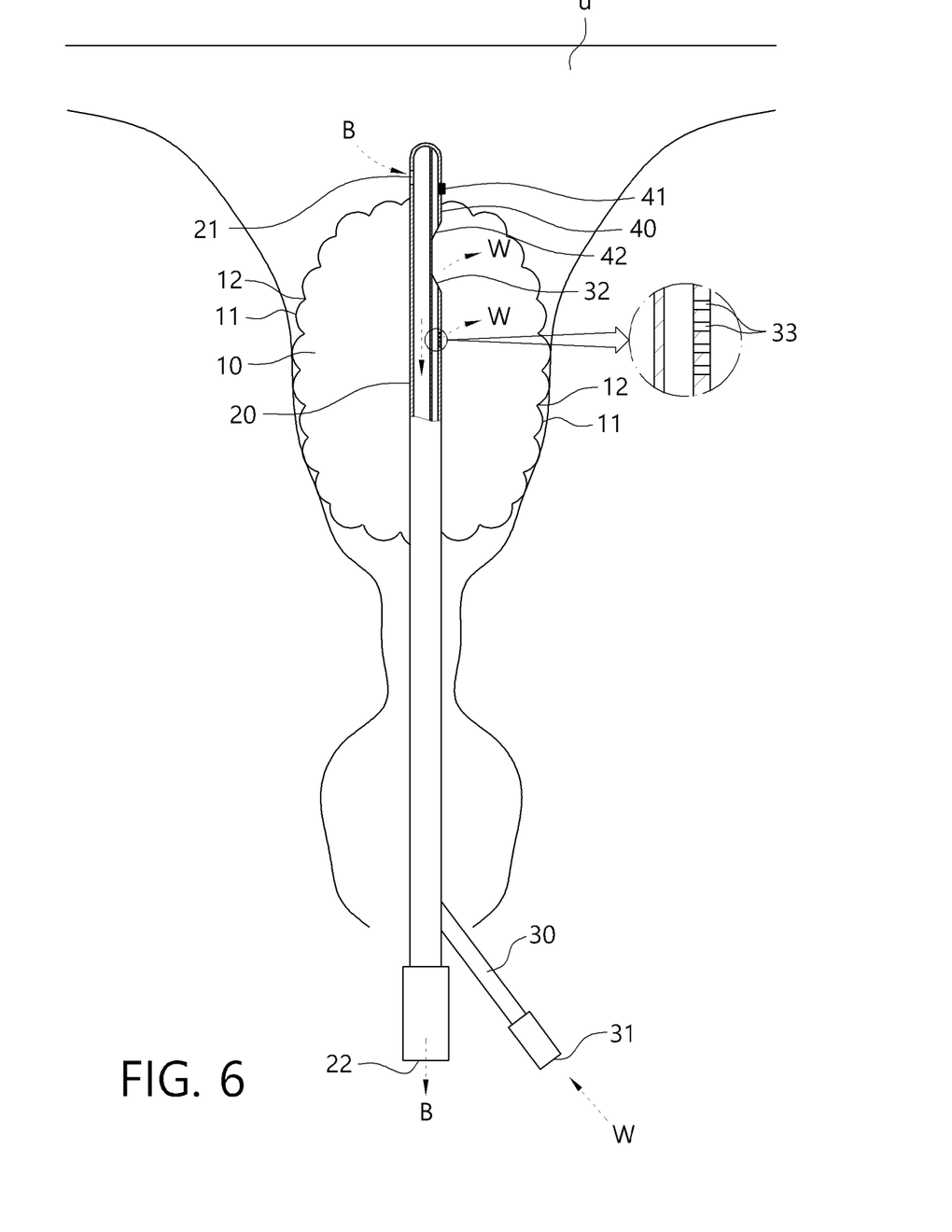
FIG. 6 is a diagram illustrating a first use state of a hemostatic device according to a second embodiment of the present invention.

FIG. 6 is a diagram illustrating a first use state of a hemostatic device according to a second embodiment of the present invention.

Referring to FIG. 6, a plurality of micropores 33 communicating with the inside of the balloon 10 may be provided in an upper section of the fluid flow pipe 30 disposed inside the balloon 10. That is, there is a difference in that the hemostatic device according to the second embodiment of the present invention has a plurality of micropores 33 in the upper section of the fluid flow pipe 30 disposed inside the balloon 10, compared to the hemostatic device according to the first embodiment of the present invention.

When the fluid W is injected through the fluid flow pipe 30, the plurality of micropores 33 allow a portion of the fluid W introduced through the first inlet/outlet 31 to flow out into the inside of the balloon 10 before reaching the second inlet/outlet 32, thereby increasing the efficiency of fluid W injection.

In addition, when the hemostatic device is removed, the fluid W inside the balloon 10 may be discharged not only through the second inlet/outlet 32 of the fluid flow pipe 30, but also through the plurality of micropores 33. The fluid entering the fluid flow pipe 30 through the plurality of micropores 33 and the second inlet/outlet 32 may be discharged to the outside through the first inlet/outlet 31 of the fluid flow pipe 30.

Figure 7:
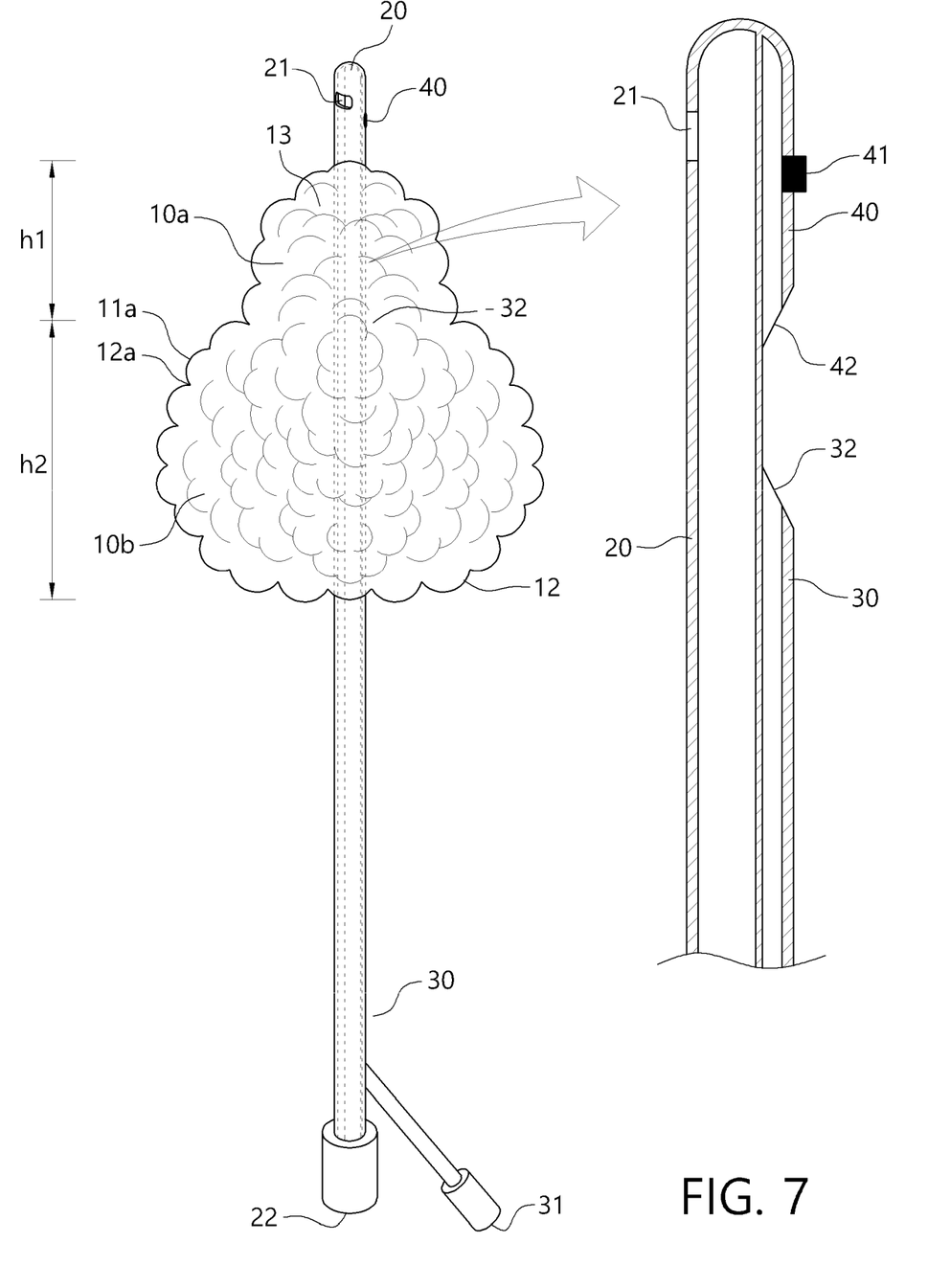
FIG. 7 is a configuration diagram of a hemostatic device according to a third embodiment of the present invention.

FIG. 7 is a configuration diagram of a hemostatic device according to a third embodiment of the present invention.

Referring to FIG. 7, the hemostatic device according to the third embodiment of the present invention has a different shape of balloon 10 compared to the hemostatic device according to the first embodiment of the present invention. Except for this, the rest of the configuration is the same as described above in relation to the first embodiment of the present invention. Therefore, only the shape of the balloon 10 of the hemostatic device according to the third embodiment of the present invention will be described below.

In the third embodiment of the present invention, the balloon 10 includes a wide portion 10b formed to expand outwardly larger than the upper portion when the balloon is expanded by the fluid W. That is, the balloon 10 includes a wide portion 10b having a relatively larger width and a narrow portion 10a having a relatively small width formed at the upper end of the wide portion 10b.

In this case, as in the first embodiment of the present invention, a plurality of protrusions 11a and 11b and concave portions 12a and 12b are formed on the outer surfaces of the narrow portion 10a and the wide portion 10b, respectively.

In the case of bleeding due to poor contraction of the uterus, it is necessary to compress the inside of the uterus as a whole, so the shape of the balloon 10 is preferably an ellipsoid as a whole. However, to stop intrauterine hemorrhage due to placenta previa or placenta accreta, it is necessary to intensively press the lower part of the uterus. The third embodiment of the present invention can be used when the need for compression to the lower part of the uterus is greater.

In the third embodiment of the present invention, the wide portion 10b may be formed in a ratio of 1/2 to 2/3 based on the height of the balloon 10 in a state in which the balloon 10 is expanded by the fluid W. In more detail, in the balloon 10 according to the third embodiment of the present invention, a section from the bottom to a certain height is formed as a wide portion 10b, and a section from the upper end of the wide portion 10b to the top is formed as a narrow portion 10a. In this case, the ratio of the height h1 of the wide portion 10b to the height h2 of the narrow portion 10a may be 2:1 to 3:1.

Figure 8:
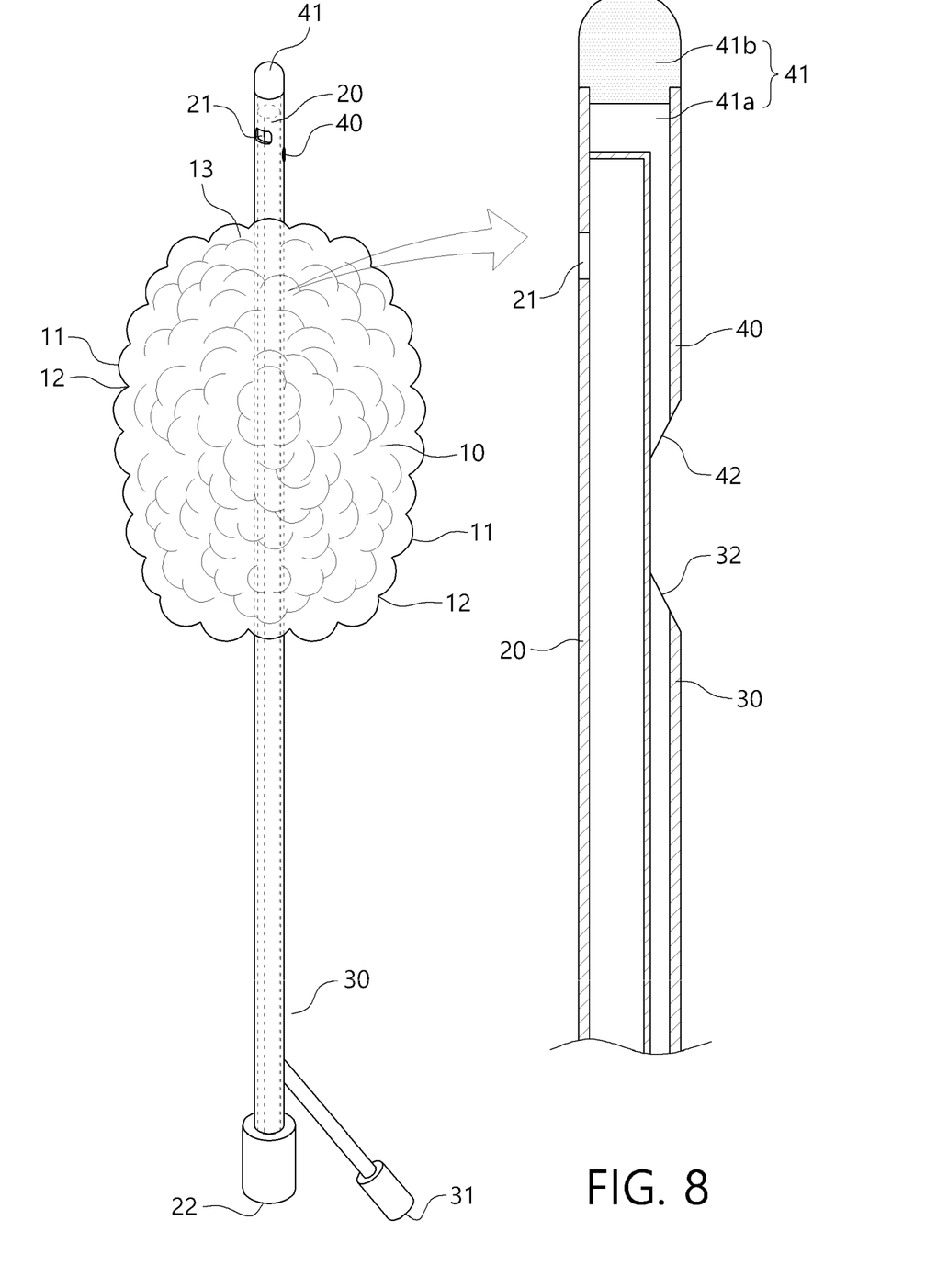
FIG. 8 is a configuration diagram of a hemostatic device according to a fourth embodiment of the present invention.
Figure 9:
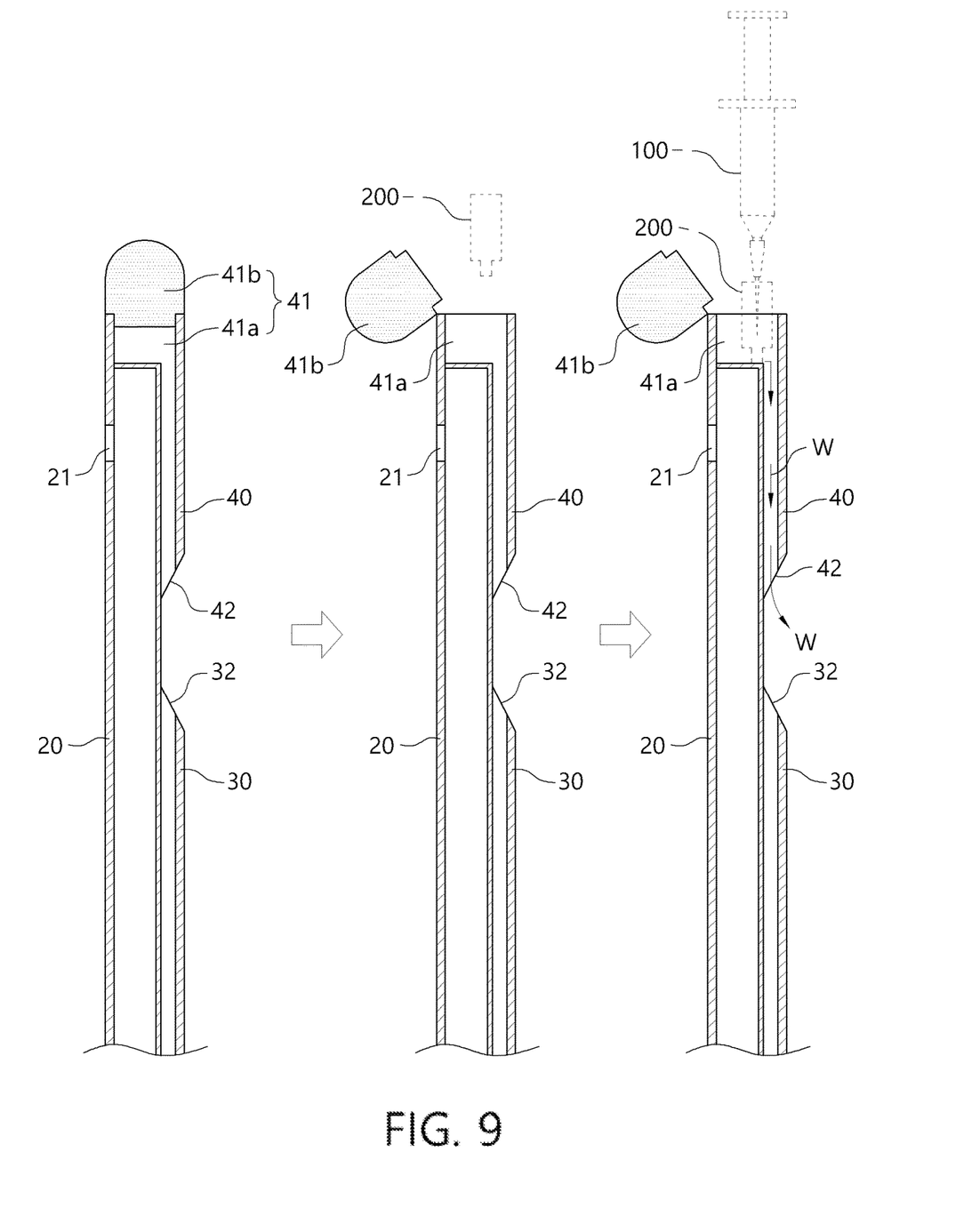
FIG. 9 is a diagram illustrating a process in which a fluid is injected into an auxiliary fluid injection pipe in the hemostatic device according to the fourth embodiment of the present invention.

FIG. 8 is a configuration diagram of a hemostatic device according to a fourth embodiment of the present invention, and FIG. 9 is a diagram illustrating a process in which a fluid is injected into an auxiliary fluid injection pipe in the hemostatic device according to the fourth embodiment of the present invention.

Referring to FIGS. 8 and 9, the hemostatic device according to the fourth embodiment of the present invention has a different injection part 41 of the auxiliary fluid injection pipe 40 compared to the hemostatic device according to the first embodiment of the present invention. Except for this, the rest of the configuration is the same as described above in relation to the first embodiment of the present invention. Therefore, only the injection part 41 of the auxiliary fluid injection pipe 40 of the hemostatic device according to the fourth embodiment of the present invention will be described below.

In the fourth embodiment of the present invention, the injection part 41 includes an injection hole 41a formed to be opened upwardly at a portion extending upwardly of the balloon 10 and a cap 41b for opening and closing the injection hole 41a.

The injection hole 41a may be formed with an enlarged diameter at an end of the portion extending upward of the balloon 10 of the auxiliary fluid injection pipe 40. In this case, the injection hole 41a may be disposed above the blood inflow hole 21. In the fourth embodiment of the present invention, the auxiliary fluid injection pipe 40 is disposed in contact with the blood discharge pipe 20, the injection hole 41a may be formed at upper side of the closed end of one end of the blood discharge pipe 20. Since the injection hole 41a is formed with an enlarged diameter in this way, when the fluid W is injected, an aid 200 for guiding the fluid supply device 100 (e.g., a syringe) may be disposed in the injection hole 41a, and so the fluid W may be more easily injected.

The cap 41b may be disposed in a form in which it can be opened when the fluid W is input and it can be closed after the fluid W is input. For example, the cap 41b may be formed of a rubber material.

Although exemplary embodiments of the present invention have been described, the spirit of the present invention is not limited to the embodiments set forth herein. Those of ordinary skill in the art who understand the spirit of the present invention may easily propose other embodiments through supplement, change, removal, addition, etc. of elements within the same spirit, but the embodiments will be also within the scope of the present invention.

What is claimed is:

1. A hemostatic device comprising:
a balloon which is expanded by a fluid supplied therein;
a blood discharge pipe which comprises a blood inflow hole at one end and the other end of the blood discharge pipe extends through a lower end of the balloon wherein an upper section of the blood discharge pipe is surrounded by the balloon;
a fluid flow pipe communicating with the inside of the balloon for supplying or discharging the fluid and extending to a lower side of the balloon; and
an auxiliary fluid injection pipe communicating with the inside of the balloon for supply of the fluid and extending upward of the balloon;
wherein the balloon comprises a plurality of protrusions that are formed to protrude outward when the balloon is expanded by the fluid,
the auxiliary fluid injection pipe has an openable and closeable injection part at a portion extending upwardly of the balloon,
the injection part has: an injection hole formed to be opened upwardly at the portion extending upwardly of the balloon; and a cap for opening and closing the injection hole.

2. The hemostatic device of claim 1, wherein the plurality of protrusions are formed to have a hemispherical shape in an expanded state of the balloon.

3. The hemostatic device of claim 1, wherein the plurality of protrusions are formed to have a polygonal shape in an expanded state of the balloon.

4. The hemostatic device of claim 1, wherein the plurality of protrusions are formed to have a honeycomb shape in an expanded state of the balloon.

5. The hemostatic device of claim 1, wherein the balloon comprises a concave portion to be formed between the plurality of protrusions to allow blood to pool and coagulate when the balloon is expanded by the fluid.

6. The hemostatic device of claim 1, wherein an upper section of the fluid flow pipe is disposed inside the balloon and a plurality of micropores communicating with the inside of the balloon is provided in the upper section of the fluid flow pipe.

7. The hemostatic device of claim 1, wherein the balloon comprises a wide portion formed to expand outwardly larger than an upper portion when the balloon is expanded by the fluid.

8. The hemostatic device of claim 7, wherein the wide portion is formed in a ratio of 1/2 to 2/3 based on the height of the balloon in a state in which the balloon is expanded by the fluid.

9. The hemostatic device of claim 1, wherein the fluid flow pipe is disposed in contact with one side of the blood discharge pipe over a certain section from the inside of the balloon, and said section is from the lower end of the balloon to the lower side.

* * * * *